United States Patent [19]

Piche et al.

[11] Patent Number: 5,433,112
[45] Date of Patent: Jul. 18, 1995

[54] ULTRASONIC CHARACTERIZATION OF POLYMER MELTS UNDER PROCESSING CONDITIONS

[76] Inventors: Luc Piche, 428 Cherrier, Montreal, Quebec, Canada, H2L 1G9; André Hamel, 4035 Boul. Westley, St-Hubert, Quebec, Canada, J3Y 2T1; Richard Gendron, 35 De L'Aqueduc #5, Varennes, Quebec, Canada, J3X 1P4; Michel Dumoulin, 502 Des Falaises, Mont St-Hilaire, Quebec, Canada, J3H 5R7; Jacques Tatibouet, 6680, De Lanaudière, Montreal, Quebec, Canada, H2G 3A9

[21] Appl. No.: 952,979

[22] Filed: Sep. 29, 1992

[51] Int. Cl.⁶ .................. G01N 29/18; G01N 29/20
[52] U.S. Cl. .................. 73/597; 73/54.41; 73/599; 73/644
[58] Field of Search .............. 73/597, 599, 644, 629, 73/628, 632, 571, 609, 64.42, 64.53, 54.41

[56] References Cited

U.S. PATENT DOCUMENTS

| | | | |
|---|---|---|---|
| 4,015,470 | 4/1977 | Morrison | 73/64.53 |
| 4,509,360 | 4/1985 | Erwin et al. | 73/599 |
| 4,559,810 | 12/1985 | Hinrichs et al. | 73/54.41 |
| 4,677,842 | 7/1987 | Piché | 73/32 A |
| 4,754,645 | 7/1988 | Piché et al. | 73/597 |
| 5,170,667 | 12/1992 | Takeuchi et al. | 73/597 |

FOREIGN PATENT DOCUMENTS

2167185 5/1986 United Kingdom ............... 73/64.53

OTHER PUBLICATIONS

Hunston, Donald L., "Determination of the High Frequency Viscoelastic Properties of Polymers Using Shear Mode Strip Delay Lines", pp. 201–210.

William H. Press et al., "Numerical Recipes", Cambridge University Press, 1986, pp. 381–416.

R. Gendron et al., "Material Characteristics Oriented Computer Control of Extrusion–Part 1", Conference Proceedings of ANTEC'91: 49th Annual Technical Conference of the Society of Plastics Engineers, May 1991, vol. XXXVII, pp. 958–963.

R. Gendron et al., "Extruder Control via On-Line Product Characteristics Monitoring", Program and Abstracts of the 7th Annual Meeting of the Polymer Processing Society, Apr. 1991, pp. 252–253.

*Primary Examiner*—Hezron E. Williams
*Assistant Examiner*—Nashmiya Ashraf
*Attorney, Agent, or Firm*—Swabey Ogilvy Renault

[57] ABSTRACT

A method and apparatus for ultrasonically characterizing a polymer melt flowing in a predetermined direction between two opposed parallel surfaces spaced from one another to define a gap filled with polymer are disclosed. Ultrasonic pulses are propagated through the polymer melt between the two surfaces in a direction normal to the direction of flow for interaction with the polymer, the ultrasonic pulses having a duration such as to prevent successive echoes from overlapping with one another while reverberating between the two surfaces. The time delay between two echoes exiting from the polymer melt and generated from each pulse having interacted with the polymer is continuously monitored while simultaneously monitoring amplitude variations of the two echoes, to provide output signals representative of ultrasonic velocity and attenuation in the polymer melt. These output signals are processed to obtain data comprising ultrasonic velocity and attenuation values measured simultaneously as a function of time. The data is then processed to derive quantitative information relating to viscoelastic properties, structure or composition of the polymer, which can be used as input data in a closed-loop process control system.

8 Claims, 9 Drawing Sheets

ULTRASONIC CHARACTERIZATION OF POLYMER MELTS UNDER PROCESSING CONDITIONS

BACKGROUND OF THE INVENTION

The present invention relates to a method and apparatus for the ultrasonic characterization of polymer melts under processing conditions. More particularly, the invention is directed toward monitoring changes in viscoelastic properties, structure and composition of flowing polymer melts during processing.

The ever increasing need for high quality products puts strong pressure on improving process control systems. This is clearly illustrated by the large number of attempts to monitor polymer properties during processing. On-line or side-stream rheometers have been developed to monitor viscoelastic properties of flowing polymer melts and to use these properties to control the process. Apart from problems inherent to mechanical devices, there are also a number of disadvantages associated with this test method. For example, only part of the flowing polymer is tested and the sampled polymer stream may not be representative of the main stream. In addition, the sampled stream will have a different shear history than the main stream.

Ultrasounds have found numerous uses in very widely different fields of application, in particular to characterize polymers, both in the solid and molten states. For instance, the ultrasonic characterization of polymers under simulated processing conditions has been described in U.S. Pat. No. 4,754,645. According to this patent, a sample of a polymer is held in confinement between two axially aligned buffer rods having opposed parallel end surfaces spaced from one another to define a gap filled with the polymer sample, the polymer sample being acoustically coupled to the opposed end surfaces of the buffer rods. Ultrasonic waves are transmitted through one of the buffer rods in a direction toward the polymer sample for interaction therewith, and the polymer sample is subjected to controlled temperature or pressure variations over a predetermined period of time, the variation in temperature or pressure being effected via the buffer rods. Phase and amplitude variations of the ultrasonic waves having interacted with the polymer sample are continuously monitored as well as thickness variations of the polymer sample, over the predetermined period of time, to obtain data comprising phase, amplitude and thickness values measured as a function of temperature or pressure and time. The data is then processed to derive characteristic parameters providing both a thermodynamic and viscoelastic characterization of the polymer.

The properties of polymers during actual processing, on the other hand, are known to be highly dependent on flow conditions, i.e., flow velocity, shear rate, pressure and temperature. The apparatus described in aforementioned patent is capable of simulating only the temperature and pressure conditions normally encountered in actual processing, and is thus limited to measuring static properties of the polymers as opposed to flow properties during processing operations.

In U.S. Pat. No. 4,509,360, on the other hand, an acoustical technique has been proposed for the on-line measurement of particle dispersion in polymer melts. The technique is based on the use of a cylindrical quartz lens mechanically coupling a piezoelectric transducer to the polymer melt. A repetitive, broadband, ultrasonic wave is produced by the transducer and is sent into the lens. The ultrasonic wave meets a spherical dimple at the end of the lens which focuses a portion of it into a diffraction limited spot or interrogation zone within the polymer melt. Unmixed or agglomerated particles in the melt passing through this zone can be detected by measuring changes in the back scattered wave which is monitored by the transducer.

Since use is made of a focussing acoustic lens, the technique described in U.S. Pat. No. 4,509,360 is limited to measuring only properties at the surface or in a very restricted volume of the polymer melt, and thus does not account for the overall properties of the bulk material. The technique does not permit measuring or monitoring the viscoelastic behavior which is intimately associated with the bulk properties. The technique also relies on a special or particular geometry of the acoustic lens which perturbates the flow characteristics and therefore renders it unsuitable for use in actual processing devices.

SUMMARY OF THE INVENTION

It is therefore an object of the present invention to overcome the above drawbacks and to provide a method and apparatus for the ultrasonic characterization of polymer melts under processing conditions.

According to one aspect of the invention, there is thus provided a method of ultrasonically characterizing a polymer melt flowing in a predetermined direction between two opposed parallel surfaces spaced from one another to define a gap filled with polymer, which comprises the steps of:

a) propagating ultrasonic pulses through the polymer melt between the two surfaces in a direction normal to the direction of flow for interaction with the polymer, the ultrasonic pulses having a duration such as to prevent successive echoes from overlapping with one another while reverberating between the two surfaces;

b) continuously monitoring time delay between two echoes exiting from the polymer melt and generated from each pulse having interacted with the polymer while simultaneously monitoring amplitude variations of the two echoes, to provide output signals representative of ultrasonic velocity and attenuation in the polymer melt;

c) processing the output signals of step (b) to obtain data comprising ultrasonic velocity and attenuation values measured simultaneously as a function of time; and d) processing the data obtained in step (c) to derive quantitative information relating to viscoelastic properties, structure or composition of the polymer.

The present invention also provides, in another aspect thereof, an apparatus for carrying out a method as defined above. The apparatus of the invention comprises a housing having a fluid passageway through which the polymer melt to be characterized flows in a predetermined direction, the passageway being defined between two opposed parallel surfaces spaced from one another to form a gap adapted to be filled with polymer, and means for propagating ultrasonic pulses through the polymer melt between the two surfaces in a direction normal to the direction of flow for interaction with the polymer, the ultrasonic pulses having a duration such as to prevent successive echoes from overlapping with one another while reverberating between the two surfaces. Monitoring means are provided for continuously monitoring time delay between two echoes exiting from the polymer melt and generated from each pulse having interacted with the polymer, and for simultaneously monitoring amplitude variations of the two echoes, to provide output signals representative of ultrasonic velocity and attenuation in the polymer melt. The apparatus further includes signal processing means operatively connected to the monitoring means for processing the output signals to obtain data comprising ultrasonic velocity and attenuation values measured simultaneously as a function of time, and data processing means connected to the signal processing means for processing the data to derive quantitative information relating to viscoelastic properties, structure or composition of the polymer.

Simultaneous measurement of wave velocity and attenuation provides an entire characterization of the ultrasonic wave propagation through the polymer melt. In polymer melts, the formalism used for viscoelastic fluids can be used and in this case, propagation of longitudinal waves leads to the longitudinal modulus, $L^*$, which results from the linear combination of the bulk, $B^*$, and the shear, $G^*$, moduli:

$$L^* = B^* + 4G^*/3 \qquad (1)$$

$L^*$ can also be expressed as:

$$L^* = L' + iL'', \qquad (2)$$

where $L'$ and $L''$, respectively the storage and loss moduli, can be related to density $\rho$, velocity $v$, attenuation $\alpha$, and frequency $\omega = 2\pi f$, through the following equations:

$$L' = \rho v^2 \qquad (3)$$

$$L'' = (2 \rho \alpha v^3)/\omega \qquad (4)$$

Knowledge of velocity leads to elastic, or storage, information ($L'$), but combination of both velocity and attenuation gives complementary information on inelastic, or loss, behavior ($L''$) of the polymer melt. Since a flowing melt may be subjected to extremely fast changes in its properties due to flow perturbation, variation in operating conditions, feed modification, etc, simultaneous measurement of v and $\alpha$ are prerequisite for instantaneous, valid information on structure, composition and viscoelastic properties of the melt.

The expression "viscoelastic properties" as used herein means information about the deformability response of a material that shows elastic (reversible deformation) and flow or viscous (irreversible deformation) behavior, when subjected to stress. This response can vary with pressure, temperature and flow conditions of the polymer melt.

From the simultaneously measured values of velocity and attenuation, it is also possible to derive information concerning the structure of virgin polymers, that is, molecular weight and polydispersity, as well as the composition of filled polymers and polymer blends, that is, the concentration, size and dispersion of fillers in the case of filled polymers and the concentration ratio of constituent polymers in the case of polymer blends. Such information can then be used as input data in a closed-loop process control system.

BRIEF DESCRIPTION OF THE DRAWINGS

Further features of the invention will become more readily apparent from the following description of preferred embodiments as illustrated by way of example in the accompanying drawings, in which.

DESCRIPTION OF PREFERRED EMBODIMENTS

Figure 1:
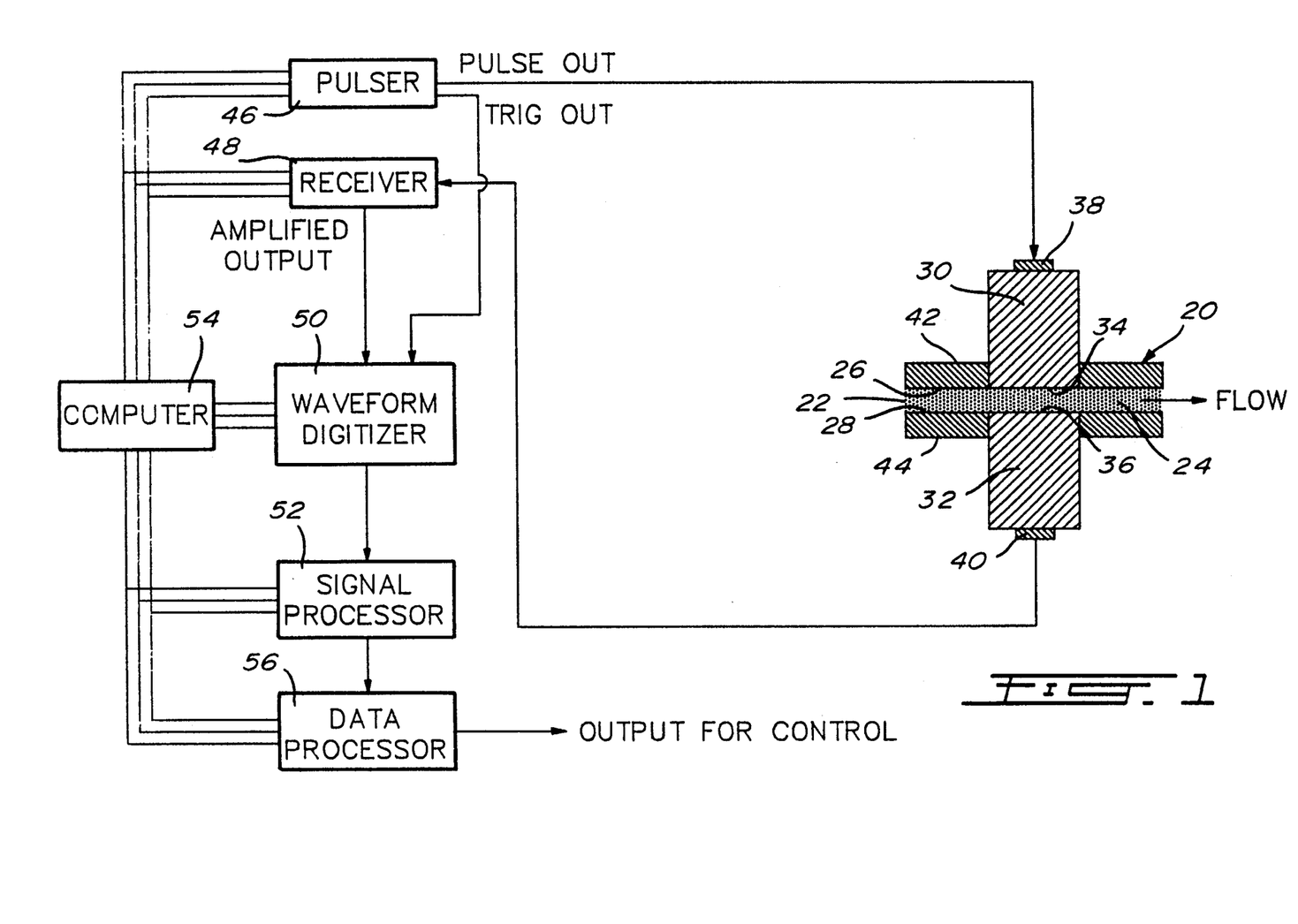
FIG. 1 is a schematic diagram of an apparatus according to a preferred embodiment of the invention, for ultrasonically characterizing polymer melts where the attenuation is less than 40 dB/cm.

Referring first to FIG. 1, there is illustrated an apparatus for ultrasonically characterizing a polymer melt, comprising a housing 20 having a fluid passageway 22 through which the polymer melt 24 to be characterized flows in the direction represented by the arrow, the passageway 22 being defined between two opposed parallel surfaces 26 and 28. Two axially aligned buffer rods 30 and 32 extend into the housing 20. The buffer rods 30,32 have opposed parallel end surfaces 34,36 which are spaced from one another to define a gap filled with the polymer under investigation. The end surfaces 34,36 of the buffer rods 30,32 are flush with the upper and lower inner surfaces 26,28, respectively, of the housing 20 in order to not disturb the normal conditions of flow and not create additional turbulence at the interfaces. The buffer rods 30 and 32 have identical lengths and their longitudinal axis extends normal to the direction of flow of the polymer melt.

Two broadband piezoelectric transducers 38 and 40 are acoustically coupled with the buffer rods 30 and 32. The transducer 38 acts as an emitting transducer for transmitting pulsed ultrasonic waves through the buffer rod 30 for interaction with the polymer melt 24 flowing between the end surfaces 34,36 of the buffer rods 30,32, whereas the transducer 40 acts as a receiving transducer for receiving via the buffer rod 32 the ultrasonic waves having interacted with the polymer. In addition to guiding the ultrasonic waves, the buffer rods 30,32 thermally isolate the transducers 38,40 from the polymer melt 24. Where high-temperature transducers are used, it is possible to mount such transducers directly on the outer surfaces 42,44 of the housing 20 using an appropriate acoustic bond, without having recourse to buffer rods for acoustically coupling the transducers with the polymer melt. Examples of suitable high-temperature transducers which may be used at temperature up to 500° F. (260° C.) are those sold under the trademark ETALON by Etalon Inc.

Figure 2A:
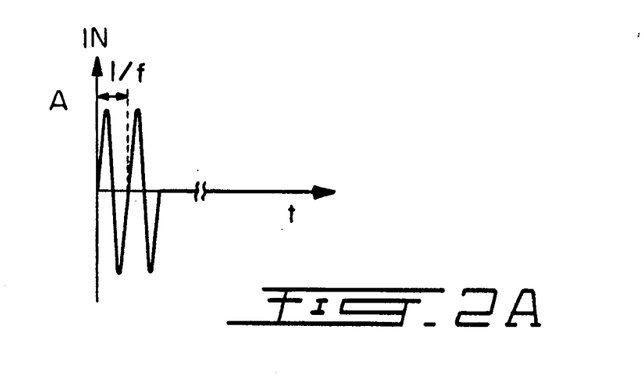
FIG. 2A is a waveform illustration of the acoustic signal entering the polymer melt.

The repetitive electric signal required to drive the emitting transducer 38 is generated from a pulser 46. The signal is typically a spiked pulse which is sent to the transducer 38 for conversion into an ultrasonic pulse whose waveform is illustrated in FIG. 2A. The pulsed ultrasonic waves have a frequency such as to provide on one hand appropriate attenuation level in order to obtain at least two echoes exiting from the polymer melt with significant resolution in their amplitude and, on the other hand, to produce pulses having a duration such as to prevent successive echoes from overlapping with one another while reverberating between the end surfaces 34,36 of the buffer rods 30,32. For most applications involving polymer melt characterization, the frequency of the ultrasonic pulses preferably ranges from about 1 to about 10 MHz and their duration preferably ranges from about 0.5 to about 1 μs.

Figure 2B:
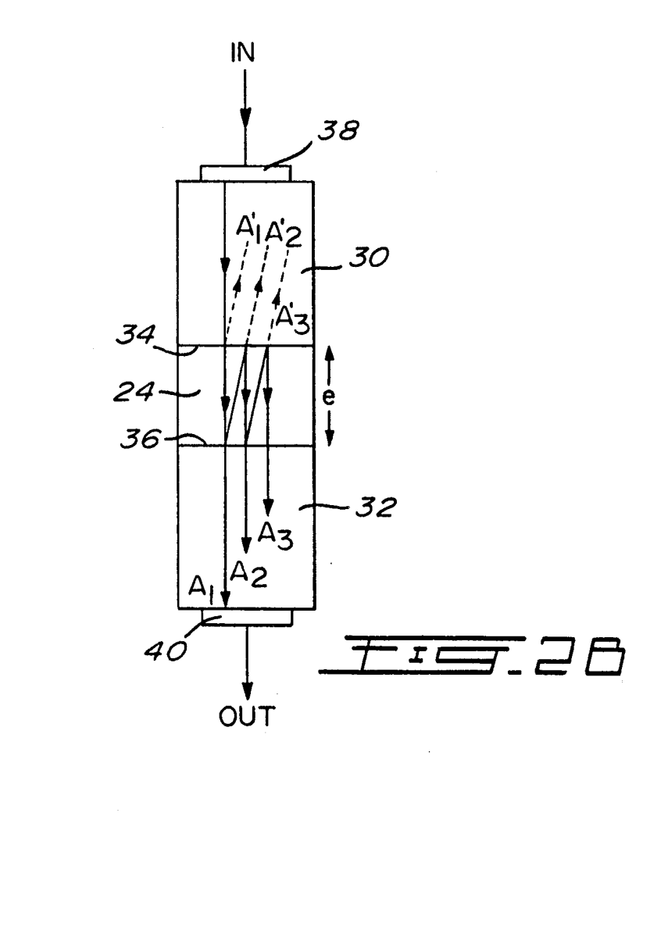
FIG. 2B schematically illustrates the propagation of an ultrasonic pulse through the polymer melt and the paths followed by the echoes generated from the pulse.
Figure 2C:
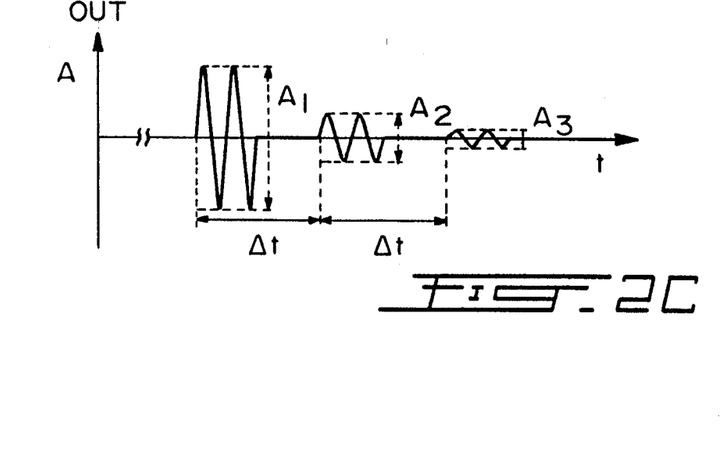
FIG. 2C is a waveform illustration of the acoustic signal exiting from the polymer melt.

As shown in FIG. 2B, the ultrasonic pulses travel through the buffer rod 30. At the interface between the buffer rod 30 and the polymer melt 24, part of the energy of each pulse is reflected giving back through the buffer rod 30 a first reflected echo of amplitude $A'_1$. The remaining energy is transmitted through the interface to the polymer melt where it interacts with the polymer. At the second interface between the polymer melt 24 and the buffer rod 32, the transmitted wave is again partially reflected to provide another reflected echo of amplitude $A'_2$. After successive reverberations between the two interfaces, a pattern of transmitted echoes of amplitudes $A_1, A_2, A_3 \ldots$, exiting from the polymer melt 24 in the same direction as the direction of pulse propagation and generated from each pulse having interacted with the polymer, is obtained. A pattern of reflected echoes of amplitudes $A'_1, A'_2, A'_3 \ldots$, exiting from the polymer melt in a direction opposite to the direction of pulse propagation, is also obtained. The waveform of the transmitted acoustic signal exiting from the polymer melt is illustrated in FIG. 2C. Each successive transmitted echo of amplitudes $A_1, A_2$ and $A_3$ is representative of a different travel length in the polymer melt. The time delay $\Delta t$, measured as the time elapsed between the onset of any two successive transmitted echoes exiting from the polymer melt, is equivalent to the travel time taken by the transmitted pulse that has propagated over the travel length $2e$, $e$ being the width of the gap defined between the end surfaces 34,36 of the buffer rods 30,32.

The transmitted echoes exiting from the polymer melt 24 are directed along the buffer rod 32 to the receiving transducer 40 where they are detected. The electric signal exiting from the transducer 40, which is representative of ultrasonic velocity and attenuation in the polymer melt, is then amplified by a receiver 48. The amplification gain of the receiver 48 is controlled to adjust the signal output level. The amplified signal is acquired by a waveform digitizer 50 synchronized by an external trigger signal issued from the pulser 46. The sampling rate of the digitizer 50 is higher than twice the wave frequency to obtain sufficient definition on the acquired waveform. In practice, a 40 MHz acquisition rate is chosen to increase accuracy.

The digitized signal is thereafter fed to a signal processor 52 where it is processed through a correlation procedure such as that described by William H. Press et al in Numerical Recipes, pages 381–416, to obtain data comprising ultrasonic velocity and attenuation values measured simultaneously as a function of time. This procedure is well known and implies working in frequency or Fourier domain. The digitized signals issued from the transmitted echoes in function of time ($a_1(t)$, $a_2(t) \ldots$) can be combined using correlation defined as:

$$\text{Corr}(a_1(t), a_2(t)) = \int a_1(t+\tau) a_2(\tau) d\tau \quad (5)$$

The correlation is a function of time and its maximum corresponds to the time elapsed between the two signals functions $a_1(t)$ and $a_2(t)$. Calculation of such correlation functions is made easy by using Fourier Transforms. The Fourier Transform of the correlation of two functions is equal to the product of the Fourier Transform of the first function by the complex conjugate of the Fourier Transform of the second function:

$$\text{Corr}(a_1(t), a_2(t)) \Leftrightarrow A_1(\omega) A^*_2(\omega) \quad (6)$$

where $A_1(\omega)$ and $A^*_2(\omega)$ are respectively the Fourier Transform of $a_1(t)$ and the complex conjugate of the Fourier Transform of $a_2(t)$.

On an other hand, the correlation of a function with itself is called autocorrelation. In this case, relation (6) becomes:

$$\text{Corr}(a_1(t), a_1(t)) \Leftrightarrow |A_1(\omega)|^2 \quad (7)$$

Dividing correlation by autocorrelation, one obtains in the frequency domain:

$$\frac{\text{Corr}(a_1(t), a_2(t))}{\text{Corr}(a_1(t), a_1(t))} \Leftrightarrow \frac{A^*_2(\omega)}{A_1(\omega)} > \quad (8)$$

By inverse transformation of this complex function, it is easy to obtain in the time domain a maximum function value corresponding to the time delay between two successive echoes, the amplitude of this maximum giving access to the ratio of the amplitudes of the echoes. This real time digitized signal processing involves Fast Fourier Transform. Acquisition and signal processing rates are controlled by a computer 54 and can be as fast as 0.8 second.

By simultaneously monitoring the time delay between two successive echoes exiting from the polymer melt and the amplitude variations of the echoes, one can thus derive from the monitored data absolute values of ultrasonic velocity and attenuation. When characterizing polymer melts having attenuation values below 40 dB/cm, the monitoring is usually effected in transmission mode, that is, the time delay between two successive transmitted echoes and the amplitude variations thereof are simultaneously monitored. Ultrasonic velocity (v) and attenuation ($\alpha$) are respectively given by:

$$v = 2e/\Delta t \qquad (9)$$

and $$\alpha = 20 \frac{[\log(A_1/A_2)]}{2e} \qquad (10)$$

where e is the width of the gap defined between the end surfaces 34,36 of the buffer rods 30,32, $\Delta t$ is the time delay between two successive transmitted echoes, and $A_1$ and $A_2$ are the amplitudes of the two echoes.

It is also possible to effect the monitoring in reflection mode. In this case, the transducer 38 acts as both an emitting and receiving transducer, and the time delay between two successive reflected echoes and the amplitude variations thereof are simultaneously monitored.

The output data of the signal processor 52 is fed to a data processor 56 for processing the data by comparing it with a calibration reference to derive quantitative information relating to the viscoelastic properties, structure or composition of the polymer. This information can be used as input data in a closed-loop process control system.

Figure 3:
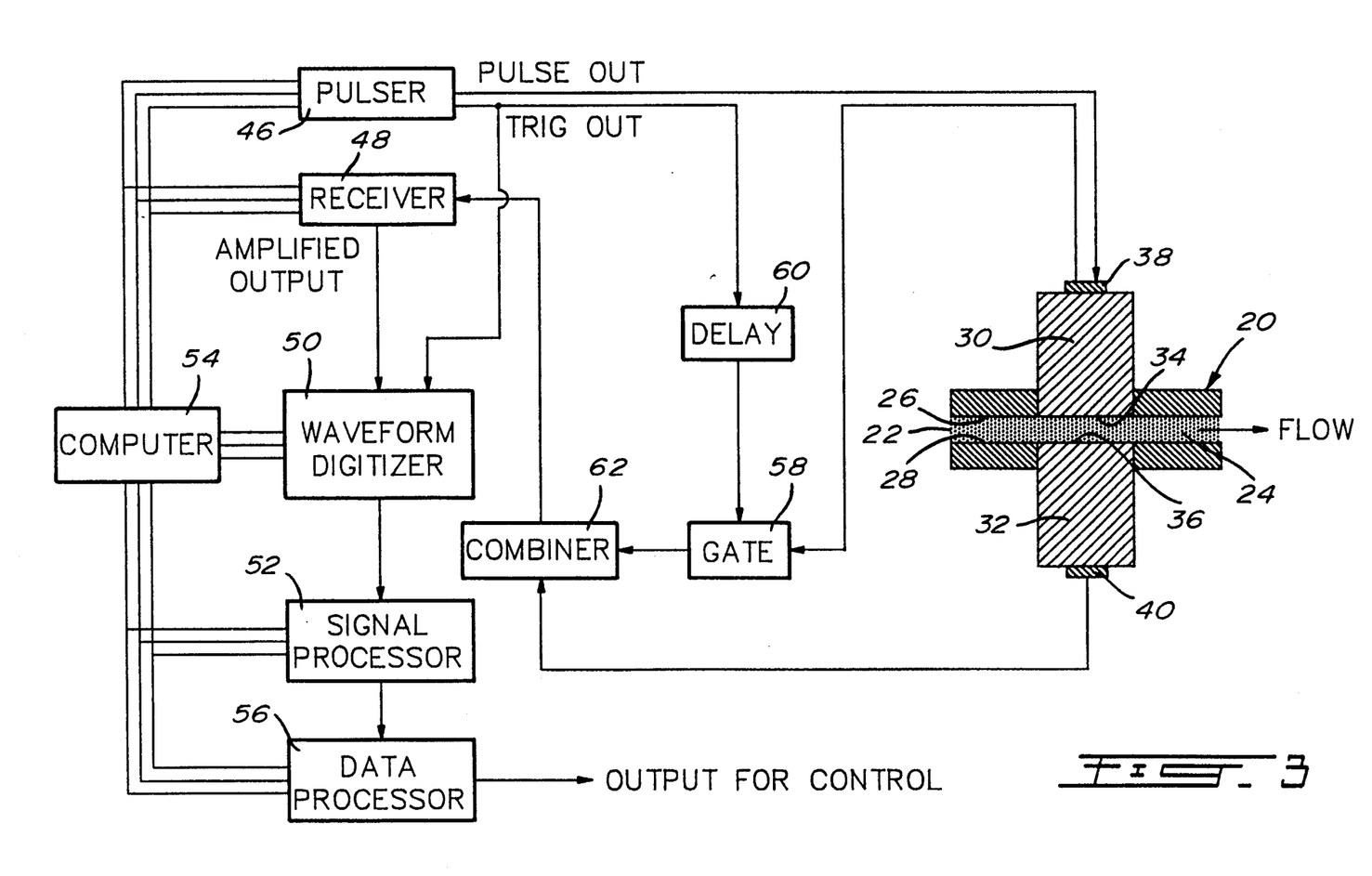
FIG. 3 is a schematic diagram of an apparatus according to another preferred embodiment of the invention, for ultrasonically characterizing polymer melts where the attenuation is greater than 40 dB/cm.

For polymer melts having attenuation values above 40 dB/cm, the second transmitted echo of amplitude $A_2$ cannot be extracted from the electronic noise level and the procedure illustrated in FIG. 3 is then used. In this case, the reflected echoes of amplitudes $A'_1$, $A'_2$, $A'_3$ ..., exiting from the polymer melt 24 in a direction opposite to the direction of pulse propagation and travelling back through the buffer rod 30, are detected by the transducer 38 which also acts as a receiving transducer when not working as an emitting transducer. The electric output signal of the transducer 38 is fed to a gate circuit 58 to select only the first reflected echo of amplitude $A'_1$. The external trigger signal of the pulser 46 is also fed to a delay circuit 60 to trigger the gate circuit 58 at an appropriate time for proper synchronization of the procedure. The gated signal is then sent to a combiner circuit 62 where it mixes with the electric output signal of the transducer 40, which is representative of the first transmitted echo of amplitude $A_1$. The composite signal is then amplified and digitized in the same way as described above in connection with FIG. 1. Signal processing is also performed in the same manner as previously described.

Considering the first reflected echo of amplitude $A'_1$ as an internal reference, the correlation procedure gives access to the time delay $\Delta t'$ between the first transmitted echo of amplitude $A_1$ and the first reflected echo of amplitude $A'_1$ and to the ratio of the amplitudes $A_1$ and $A'_1$. In this case, the ultrasonic velocity (v) and attenuation ($\alpha$) are given by:

$$V = e/\Delta t' \qquad (11)$$

and $$\alpha = \alpha_{initial} - 40 \frac{[\log(A_1/A'_1)]}{2e} \qquad (12)$$

An alternative to the determination of the attenuation is to monitor only the amplitude $A_1$ of the first transmitted echo from the autocorrelation process. In that case:

$$\alpha = \alpha_{initial} + 40 \frac{[\log(A_{1\ initial}/A_1)]}{2e} \qquad (13)$$

In equations (12) and (13), $\alpha_{initial}$ and $A_1$ initial are initial values of attenuation and amplitude of the first transmitted echo. These initial values are generally determined by using a low attenuation polymer melt prior the selected experimentation.

The following non-limiting examples further illustrate the invention.

EXAMPLE 1—FILLED POLYMER

Incorporation of calcium carbonate (Genstar Camel-Wite grade) in polypropylene (Grade 6631 from Himont) was performed using a twin-screw extruder equipped with an apparatus as shown in FIG. 3, the housing 20 being disposed between the extruder head and the die. Multiple step changes in the feeding rate of calcium carbonate, while maintaining constant the feeding rate of polypropylene, were produced in order to provide several concentration levels and to obtain a calibration curve for the ultrasonic characteristics as a function of the filler concentration. Data acquisition was done at a preset rate, and the results of ultrasonic velocity and attenuation measurements as a function of time elapsed during the experiment are illustrated in FIG. 4.

For each concentration level, extrudate was sampled and accurate concentration values were obtained from pyrolysis (ashing). For the experiment, the concentration varied from 0.0 to 62.1 wt %. From FIG. 4, the average levels of attenuation and ultrasonic velocity were determined for each step change of filler feeding rate, and the resulting values are reported in FIG. 5 as a function of the concentration of calcium carbonate. Continuous curves were thus obtained for both attenuation and ultrasonic velocity, which can be used as reference curves for the determination of the filler concentration, for a given attenuation or ultrasonic velocity value.

Figure 4:
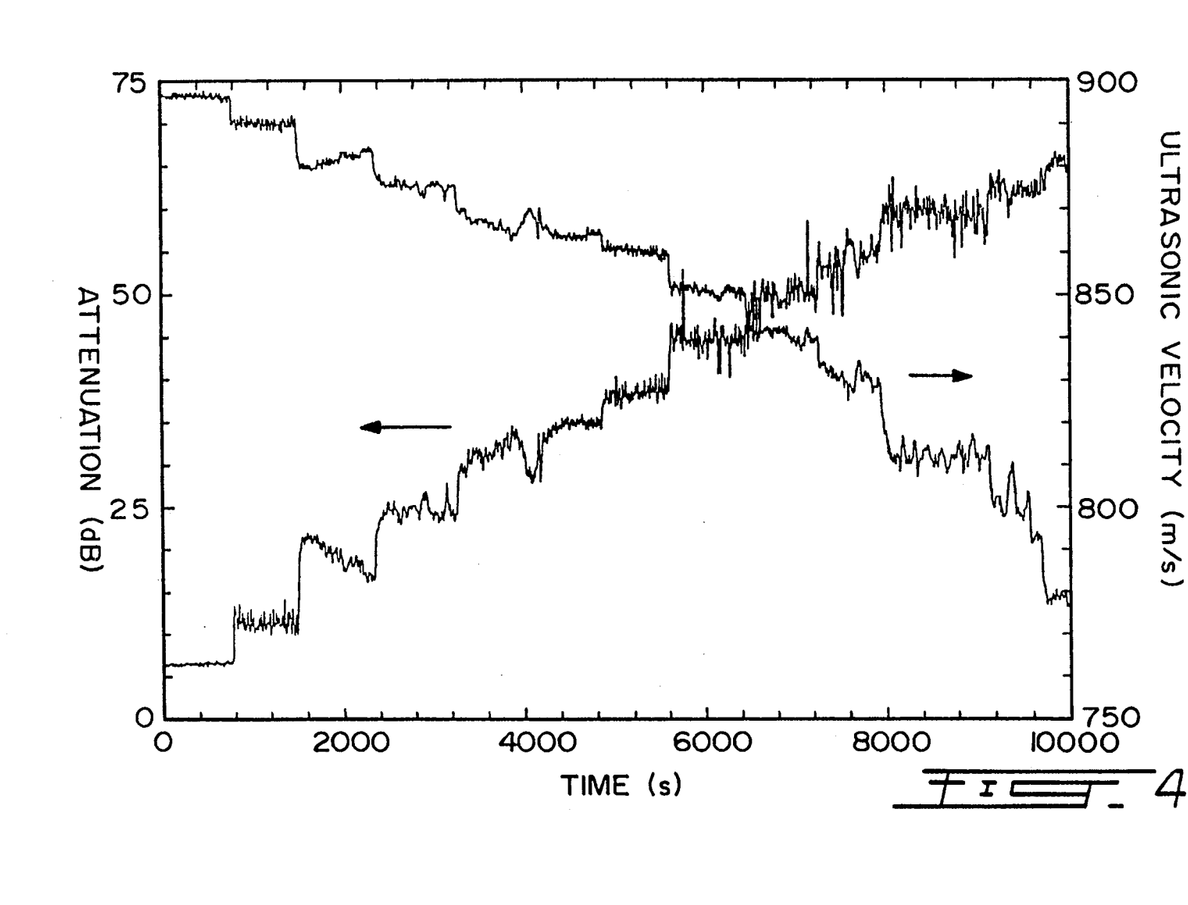
FIG. 4 is a graph showing the variation of ultrasonic velocity and attenuation as a function of time, for a filled polymer.
Figure 5:
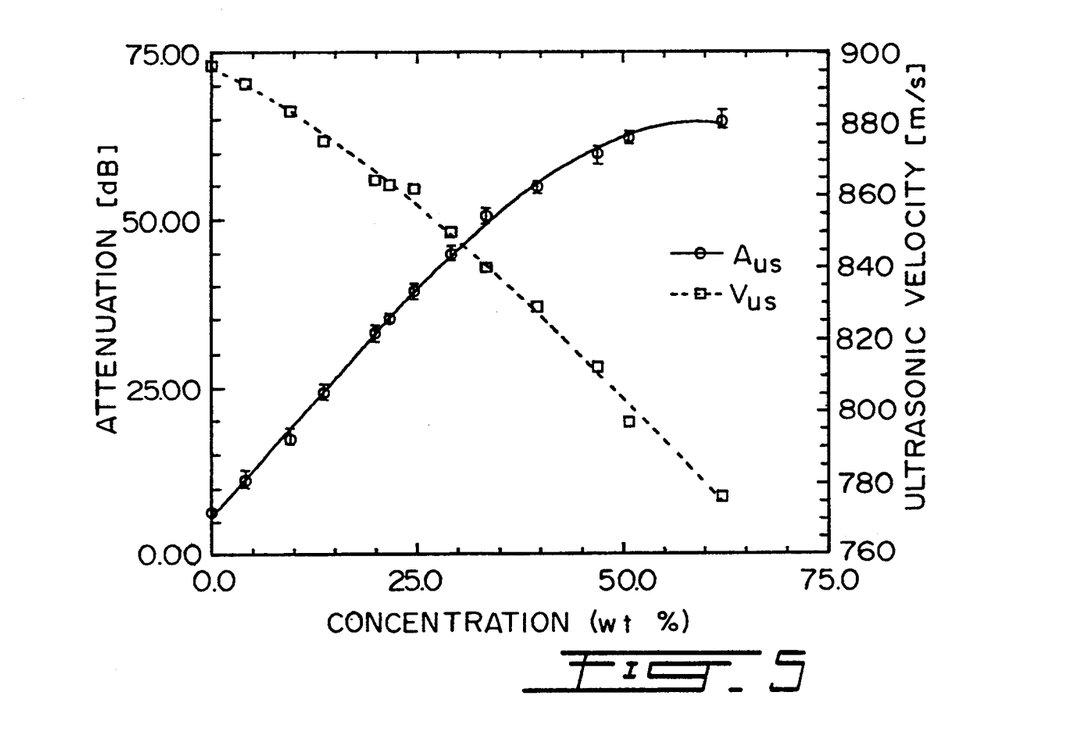
FIG. 5 is a graph showing the variation of ultrasonic velocity and attenuation as a function of the filler concentration in the filled polymer of FIG. 4.

Incertainties on attenuation values that are indicated on FIG. 5 by means of error bars are derived from the amplitude of signal noise shown in FIG. 4. This noise is expected to be correlated to fluctuations in particle size distribution and particle agglomeration, and to fluctuation in punctual concentrations.

Figure 6:
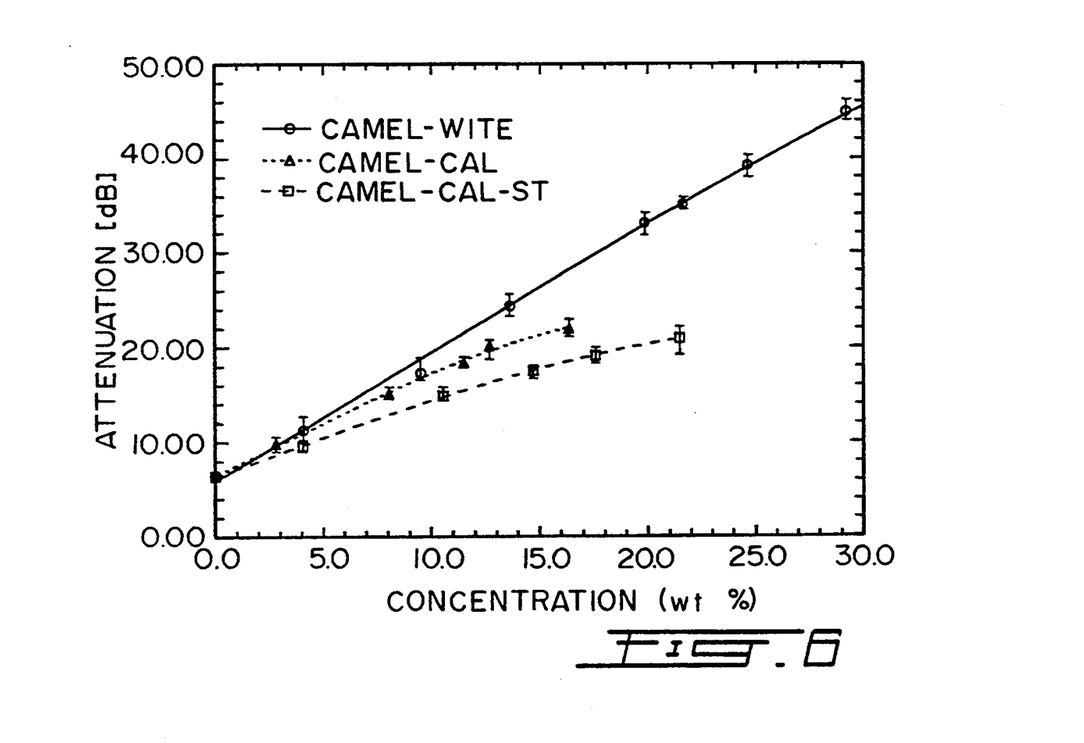
FIG. 6 is a graph showing the variation of the ultrasonic attenuation as a function of the filler concentration of filled polymers having filler particles of different dimension.

To illustrate the impact of particle dimension on the attenuation, the results obtained with the above experiment for calcium carbonate having a mean particle diameter of 3 $\mu$m (Genstar Camel-Wite grade) were compared to results obtained with calcium carbonate having a mean particle diameter of 0.7 $\mu$m (Genstar Camel-Cal grade), as shown in FIG. 6. The procedure that was followed for the determination of the calibration curve for the 0.7 $\mu$m grade was the same as for the 3 $\mu$m grade, described above. On the same FIG. 6 are also presented results obtained with a treated calcium carbonate having a mean particle diameter of 0.7 $\mu$m (Genstar Camel-Cal-ST grade), known to have a better dispersion effect of particles. Three different calibration curves were obtained, illustrating the effect of particle size and agglomeration (dispersion) on the attenuation. Similarly three different curves can also be obtained for the ultrasonic velocity as a function of filler concentration. A calibration curve should thus be made for each different grade of filler, with respect to particle size and dispersion.

Calibration curves need to be determined only if absolute concentration readings are required, as in the case of servomechanism-type of control application, wherein control set-point (expressed in % concentration) is changed from one preset value to a new operation set-point.

Figure 7:
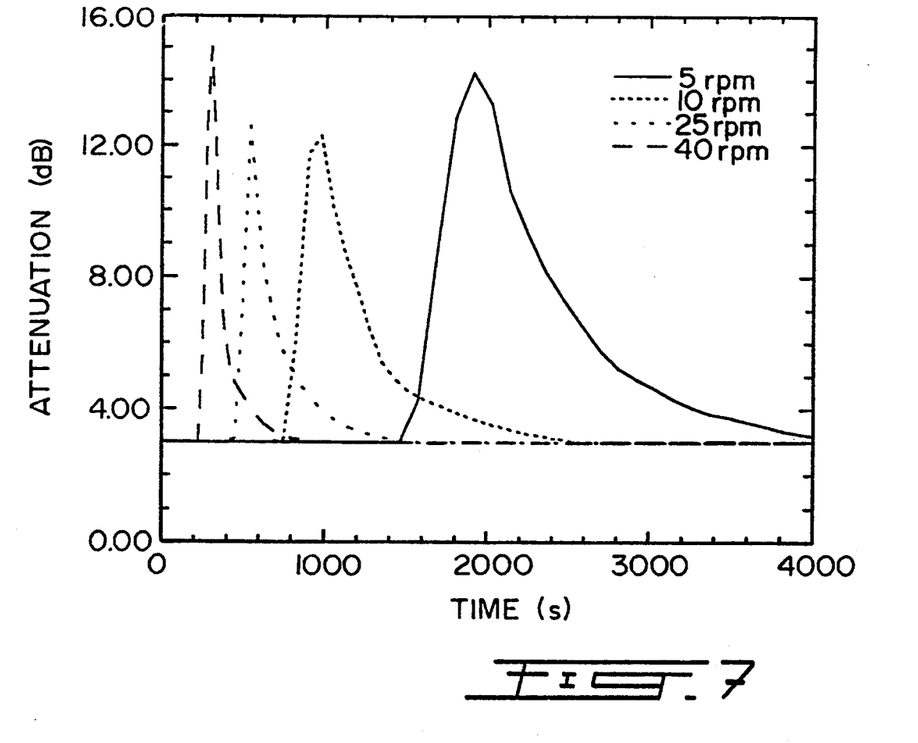
FIG. 7 is a graph showing the variation of the ultrasonic attenuation as a function of time, for an impulse injection of a filled polymer acting as a tracer in a single screw extruder at different screw speeds.

In addition to control applications for compounding processes, capability of monitoring on a real time basis the concentration of a filled polymer, related to attenuation through a given calibration curve, can be used in the determination of the residence time distribution for various polymer transformation processes, such as in a single screw extruder, as illustrated in FIG. 7. A polypropylene/calcium carbonate system was used to determine the residence time for different extrusion speeds. While processing pure polypropylene at a given screw speed, a small amount of calcium carbonate filled polypropylene was inserted in the hopper at the screw level, and ultrasonic data acquisition was started (time equals 0 sec.). After a certain delay, the calcium carbonate appeared at the location of the ultrasonic transducers, and the relative concentration of the filler was detected through the change in the amplitude of the attenuation. Time elapsed since the feeding of the small amount of filled polymer was recorded along with the attenuation amplitude, until the attenuation level returned back to its original value (pure polymer). This experiment was repeated several times with different screw speeds, and the results are reported in FIG. 7. From attenuation value distributions, mean residence times can thus be determined as a function of screw speed.

Figure 8:
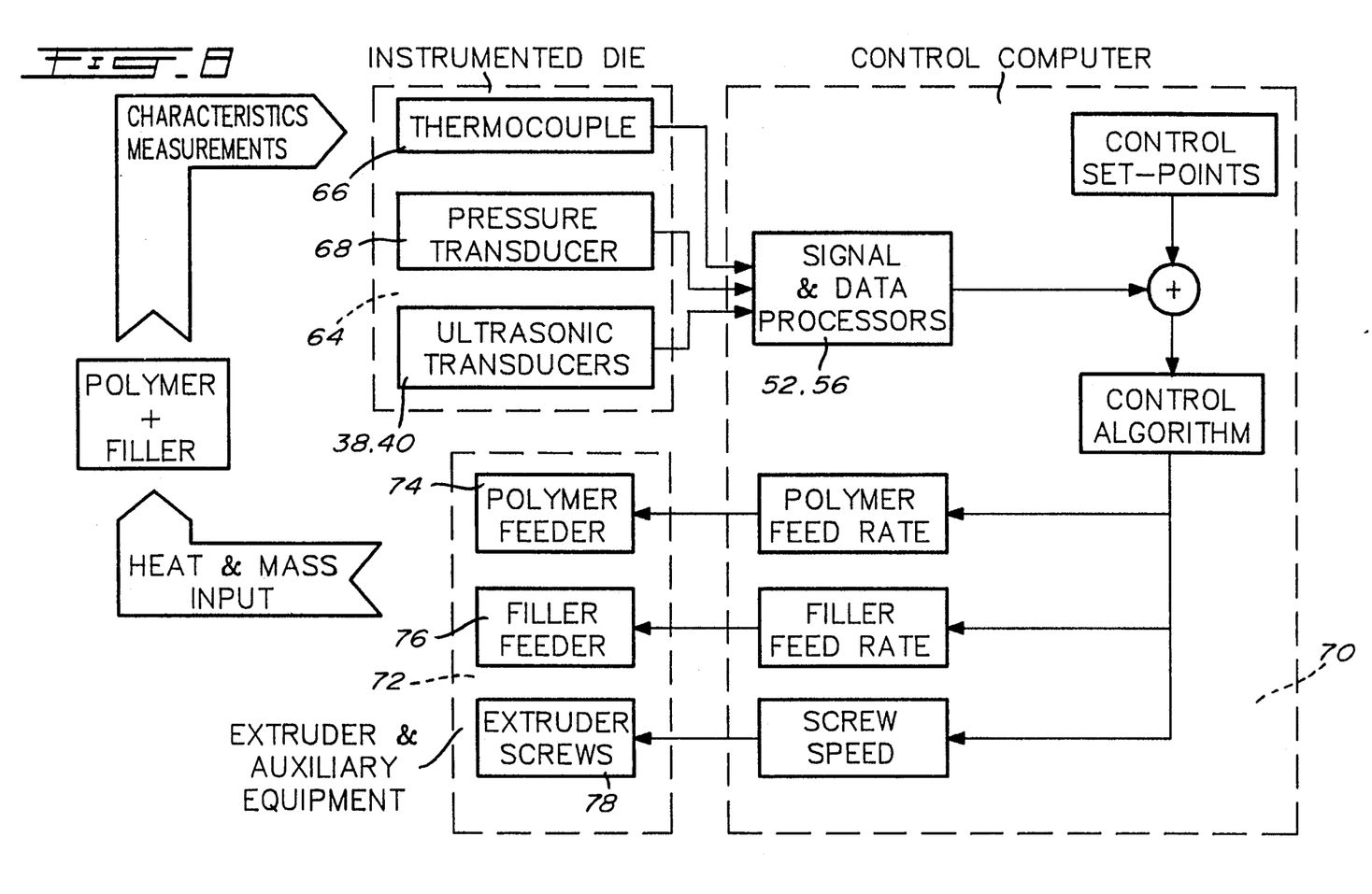
FIG. 8 is a block diagram of a closed-loop process control system for controlling the filler concentration in a filled polymer.

In first approach, for applications regarding filled polymers where simplified monitoring and control purposes are desired, attenuation should be preferred over ultrasonic velocity because of its low sensitivity to temperature and pressure fluctuations. Variations of less than ±1.5% on the attenuation reading can be anticipated for variation of ±2° C. of the polymer melt temperature, or ±0.5 MPa of the pressure at the location of the ultrasonic transducers. A more precise control scheme should however rely on a complete model based on both measurements of attenuation and ultrasonic velocity to minimize the effect of pressure and temperature in the concentration determination, as illustrated in FIG. 8. Using an instrumented die 64, the characteristics of a filled polymer were measured at the die location with the help of a melt thermocouple 66, a melt pressure transducer 68 and ultrasonic transducers 38,40. Readings were digitized and processed in the signal and data processors 52,56 to lead to attenuation and ultrasonic velocity values taking into consideration variations in the melt temperature, melt pressure, and to derive from these values the filler concentration. This concentration reading was compared to a control set-point value and offset was processed in a control algorithm in the computer 70. Control action can therefore be taken on the twin-screw extruder and auxiliary equipment 72, such as on the polymer feeder 74 or filler feeder 76 to vary the polymer feed rate or the filler feed rate and thereby vary the filler concentration value, or secondary actions may be taken on the screw speed of the extruder screws 78 to modify the melt temperature and pressure.

EXAMPLE 2—POLYMER BLEND

Figure 9:
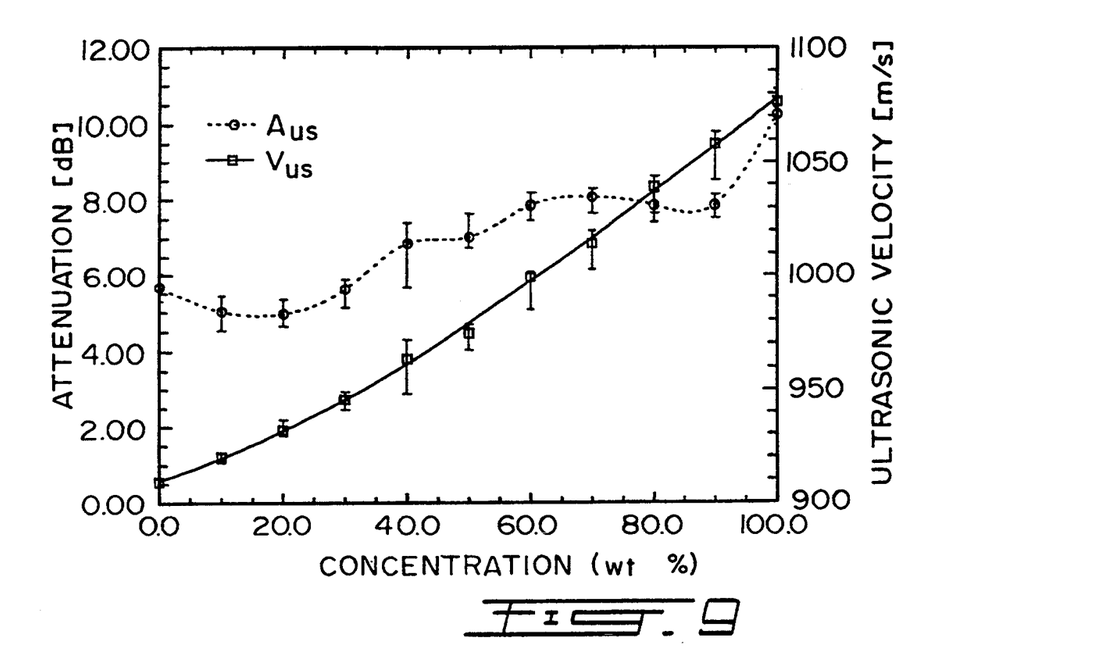
FIG. 9 is a graph showing the variation of the ultrasonic velocity and attenuation as a function of concentration, for a polymer blend.

Blending of polypropylene (grade 6631 from Himont) with polystyrene (grade 103 from Novacor) was performed using a twin-screw extruder, while monitoring the ultrasonic characteristics for multiple step changes in the concentration, from 0.0 to 100.0%. Average levels of ultrasonic velocity and attenuation as a function of concentration are shown in FIG. 9. FIG. 9 indicates that ultrasonic velocity should be used to monitor the concentration level. Giving that the discrimination on the measurement of the ultrasonic velocity was approximatively 0.5 m/s, precision on concentration was estimated to be ±0.3%.

Figure 10:
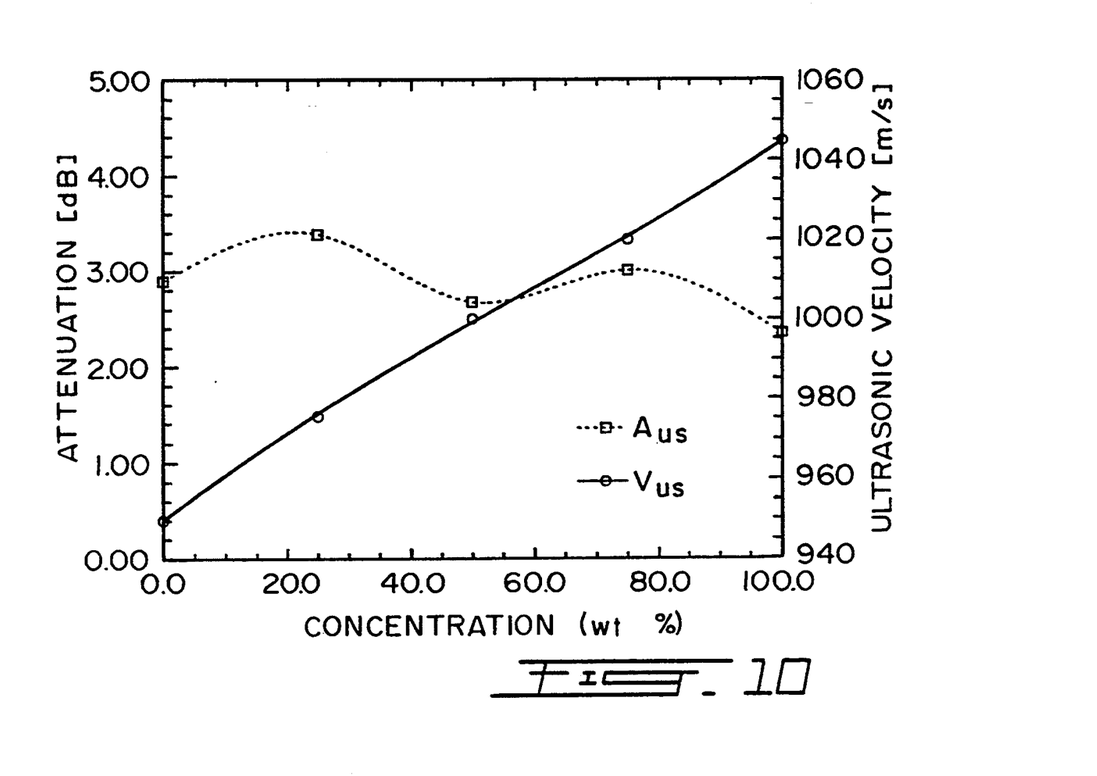
FIG. 10 is a graph similar to FIG. 9 for a different type of polymer blend.

The same type of conclusions were derived in the case where two polyolefines (polypropylene and high density polyethylene) were blended together. The results of ultrasonic velocity and attenuation measurements are reported in FIG. 10. In this case, due to the similar nature of the two polymers, precision level was decreased to ±0.6%.

Apart from the application in blending processes, one may consider the utilization of ultrasonic velocity in the domain of recycling, where consistency of unknown material can thus be on-line monitored.

EXAMPLE 3—DEGRADATION OF POLYPROPYLENE

Selective degradation of polypropylene is performed in the industry using initiators such as organic peroxides in order to produce tailored desired grades of homogeneous raw material. Polypropylene degradation follows a specific path with respect to its material structure such as average molecular weight and corresponding molecular weight distribution, where relative flowrate of peroxide added to the polypropylene is the main control variable in a continuous degradation process.

An experiment of degradation of polypropylene using peroxide was run on a single screw extruder, in order to produce different grades of polypropylene, presenting a broad variation in the molecular weight and molecular weight distribution values. Peroxide (Perkadox 14 in solution of n-heptane) was incorporated to the polypropylene (grade 6631 from Himont, MFR=2.0 dg/min.) at the beginning of the feeding zone. Accuracy in the flowrate of peroxide was assured by using a precise volumetric pump. Melt pressure and temperature in the die were monitored along with ultrasonic characteristic measurements. Pressure in the die was also held constant: the pressure reading was feedback controlled through a proportional integral derivative algorithm by modifying the screw speed, which then affected the total flowrate of polypropylene. Rheologically speaking, the shear stress $\sigma_{12}$ was held constant, and the shear rate $\dot{\gamma}$ varied according to the changes in the viscosity of the modified polymer.

The flowrate of peroxide was decreased in a step change sequence, modifying then the ratio peroxide to polypropylene, and thus varying the degree of degradation, from a low viscosity to a high viscosity polymer. Samples of the extrudate were taken for each change in the peroxide flowrate, and were analyzed to determine the paired results of average molecular weight ($M_w$) and molecular weight distribution (MWD). The results of the ultrasonic velocity measurement, obtained at a preset rate of data acquisition, are reported in FIG. 11, along with punctual measurements of molecular weight, for several step changes in the peroxide concentration, as a function of the time elapsed during the experiment.

Figure 11:
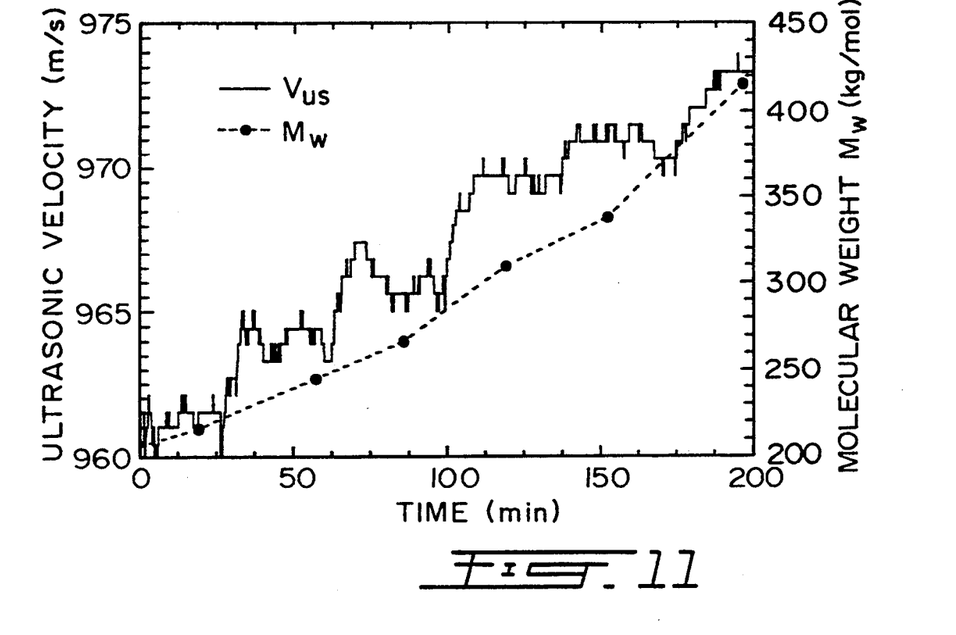
FIG. 11 is a graph showing the variation of the ultrasonic velocity and molecular weight as a function of time, in a polymer degradation process.
Figure 12:
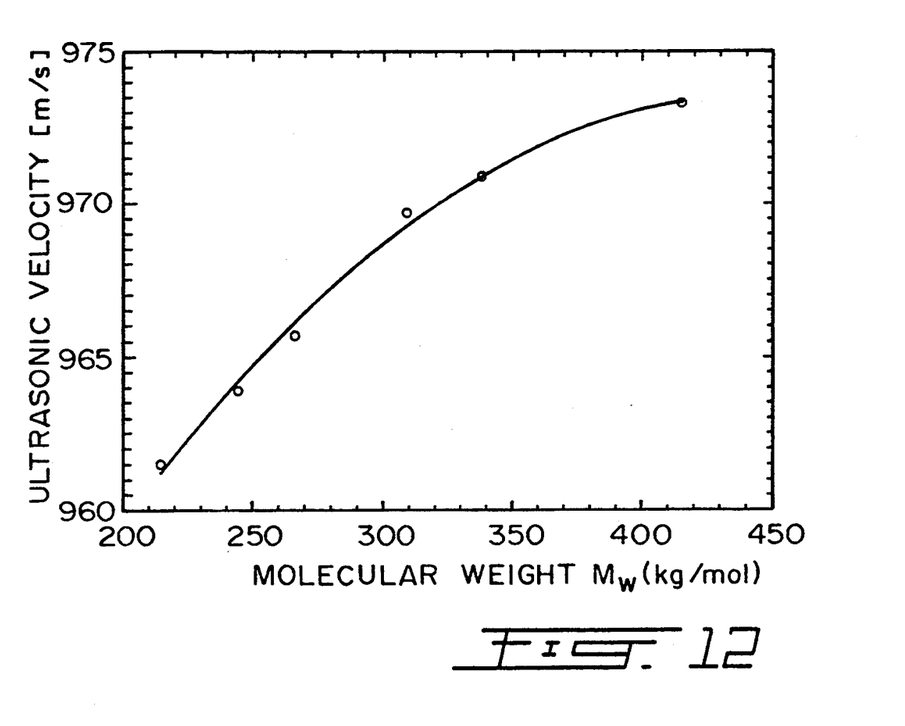
FIG. 12 is a graph showing the variation of the ultrasonic velocity as a function of molecular weight, for the polymer degradation represented in FIG. 11.

The average level of ultrasonic velocity for each step change shown in FIG. 11 and the corresponding molecular weight are reported in FIG. 12, which correspond to a continuous quadratic relationship. Ultrasonic velocity can thus be used to monitor the structural changes in the polymer, namely the molecular weight variations. With a resolution of 1.0 m/s for the ultrasonic velocity, one can detect a 5% change in the molecular weight.

We claim:

1. A method of ultrasonically characterizing a polymer melt flowing in a predetermined direction between two opposed parallel surfaces spaced from one another to define a gap filled with polymer, which comprises the steps of:
   a) propagating ultrasonic pulses through said polymer melt between said surfaces in a direction normal to the direction of flow for interaction with said polymer, said ultrasonic pulses having a duration such as to prevent successive echoes from overlapping with one another while reverberating between said surfaces, whereby the echoes generated from each pulse having interacted with said polymer include a plurality of transmitted echoes exiting from said polymer melt in the same direction as the direction of pulse propagation and a plurality of reflected echoes exiting from said polymer melt in a direction opposite to the direction of pulse propagation;
   b) continuously monitoring a time delay between a first one of said transmitted echoes and a first one of said reflected echoes while simultaneously monitoring amplitude variations of said first transmitted echo and said first reflected echo, to provide output signals representative of ultrasonic velocity and attenuation in said polymer melt;
   c) processing the output signals of step (b) to obtain data comprising ultrasonic velocity and attenuation values measured simultaneously as a function of time; and
   d) processing the data obtained in step (c) to derive quantitative information relating to viscoelastic properties, structure or composition of said polymer.

2. A method as claimed in claim 1, wherein said first transmitted echo has a predominant amplitude relative to other transmitted echoes and is detected to provide a first output signal, and wherein said reflected echoes are detected to provide a second signal which is gated to select said first reflected echo, and the gated second signal is combined with said first signal prior to processing in step (c).

3. A method as claimed in claim 1, wherein step (d) includes comparing the data obtained in step (c) with a calibration reference.

4. A method as claimed in claim 1, further including the step of using the information derived in step (d) as input data in a closed-loop process control system.

5. An apparatus for ultrasonically characterizing a polymer melt, comprising:
   a housing having a fluid passageway through which the polymer melt to be characterized flows in a predetermined direction, said passageway being defined between two opposed parallel surfaces spaced from one another to form a gap adapted to be filled with polymer;
   a first ultrasonic transducer acoustically coupled to said polymer melt for propagating ultrasonic pulses through said polymer melt between said surfaces in a direction normal to the direction of flow for interaction with said polymer, said ultrasonic pulses having a duration such as to prevent successive echoes from overlapping with one another while reverberating between said surfaces, whereby the echoes generated from each pulse having interacted with said polymer melt include a plurality of reflected echoes exiting from said polymer melt in a direction opposite to the direction of pulse propagation and a plurality of transmitted echoes exiting from said polymer melt in the same direction as the direction of pulse propagation, with a first one of said transmitted echoes having a predominant amplitude relative to other transmitted echoes;
   monitoring means for continuously monitoring time delay between two echoes exiting from said polymer melt and generated from each pulse having interacted with said polymer, and for simultaneously monitoring amplitude variations of said two echoes, to provide output signals representative of ultrasonic velocity and attenuation in said polymer melt, said monitoring means comprising a second ultrasonic transducer acoustically coupled to said polymer melt for detecting said first transmitted echo to provide a first output signal, said first transducer acting as both an emitting and receiving transducer and being operative to detect said reflected echoes to provide a second output signal, said monitoring means further including gate circuit means connected to said first transducer for gating said second output signal to select a first one of said reflected echoes and combiner circuit means connected to said second transducer and said gate circuit means for combining said first output signal with the gated second output signal, whereby to simultaneously monitor the time delay between said first transmitted echo and said first reflected echo and the amplitude variations thereof, said signal processing means being connected to said combiner circuit means for processing the combined signals;
   signal processing means operatively connected to said monitoring means for processing said output signals to obtain data comprising ultrasonic velocity and attenuation values measured simultaneously as a function of time; and
   data processing means connected to said signal processing means for processing said data to derive quantitative information relating to viscoelastic properties, structure or composition of said polymer.

6. An apparatus as claimed in claim 5, wherein said first transducer is operative to generate ultrasonic pulses having a frequency ranging from about 1 to about 10 MHz.

7. An apparatus as claimed in claim 6, wherein the ultrasonic pulses generated by said first transducer have a duration ranging from about 0.5 to about 1 $\mu$s.

8. An apparatus as claimed in claim 5, wherein said first and second transducers are acoustically coupled to said polymer melt by means of two axially aligned buffer rods each having a longitudinal axis extending normal to the direction of flow of said polymer melt, said two opposed parallel surfaces being constituted by spaced-apart opposed end surfaces of said buffer rods, said gap being defined between said end surfaces, and wherein said first and second transducers are mounted respectively at an opposite end of each said buffer rod.

* * * * *